United States Patent [19]
McCormick

[11] Patent Number: 5,461,953
[45] Date of Patent: Oct. 31, 1995

[54] MULTI-DIMENSION MICROTOME SECTIONING DEVICE

[76] Inventor: James B. McCormick, 6755 Longmeadow Dr., Lincolnwood, Ill. 60646

[21] Appl. No.: 217,957

[22] Filed: Mar. 25, 1994

[51] Int. Cl.⁶ .................................................. G01N 1/06
[52] U.S. Cl. ................. 83/36; 83/76.9; 83/412; 83/713; 83/915.5; 83/955
[58] Field of Search .............. 83/36, 76.6, 76.9, 83/412, 703, 713, 714, 915.5, 955

[56] References Cited

U.S. PATENT DOCUMENTS

| | | | |
|---|---|---|---|
| 2,643,579 | 6/1953 | Jacoby, Jr. | 83/915.5 X |
| 3,667,330 | 6/1972 | Kobernick | 83/955 X |
| 3,690,988 | 9/1972 | Ullberg . | |
| 3,699,830 | 10/1972 | Pickett | 83/13 |
| 3,727,506 | 4/1973 | Taylor et al. | 83/915.5 X |
| 3,828,641 | 8/1974 | Sitte | 83/915.5 X |
| 3,832,923 | 9/1974 | Lassmann et al. | 83/915.5 X |
| 4,208,931 | 6/1980 | Collins | 83/955 X |
| 4,502,358 | 3/1985 | Behme | 83/915.5 X |
| 4,505,175 | 3/1985 | Reichel | 83/703 |
| 4,625,608 | 12/1986 | Behme et al. | 83/713 |
| 4,700,600 | 10/1987 | Pickett | 83/165 |
| 5,092,210 | 3/1992 | Dern | 83/915.5 X |
| 5,226,335 | 7/1993 | Sitte | 83/74 |

*Primary Examiner*—Eugenia Jones
*Attorney, Agent, or Firm*—Fitch, Even, Tabin & Flannery

[57] ABSTRACT

A method and apparatus for cutting tissue sections from an organic tissue specimen to generate multiple tissue ribbons having any desired section sequencing. A three-dimensional microtome which allows relative movement between the tissue specimen and the cutting blade in three dimensions is used to generate the tissue ribbons. Preferably, the three-dimensional microtome also includes an advanceable cutting blade capable of being conveniently advanced in the direction along its length to provide a fresh cutting edge to the cutting area of the microtome.

26 Claims, 3 Drawing Sheets

MULTI-DIMENSION MICROTOME SECTIONING DEVICE

FIELD OF THE INVENTION

The present invention relates to an apparatus and method for sectioning organic tissue specimens. More particularly, the invention relates to an apparatus and method for cutting a tissue specimen into multiple tissue ribbons using a microtome.

BACKGROUND OF THE INVENTION

A microtome is a piece of precision equipment having a cutting blade for making very thin sections (1 to 15 μm) from organic tissue specimens for pathological examination. Various known microtomes have means for moving the tissue specimen and/or the cutting blade relative to each other in the direction towards and away from the cutting edge of the blade to allow intersection of the specimen with the cutting edge. Known microtomes also provide means for advancing the tissue specimen and/or the blade in a direction perpendicular to the face of the blade to allow the thickness of the slices to be controlled and to prevent contact between the specimen and the blade between cuts. Known microtomes, however, do not provide for relative movement of the blade or tissue specimen in a third direction parallel to the length of the cutting blade.

One known shortcoming of known microtomes is that consecutively sliced organic tissue sections generated at the same position along the length of the blade tend to overlap each other to form ribbons of individual tissue sections, separation of which is often tedious and time consuming. In the past, when invasive techniques involving the use of a scalpel were used by doctors to obtain samples for pathological examination, large samples of diagnostic material was routinely available and separation of each consecutively cut tissue section was less critical. With the advent of modern less-invasive methods for obtaining organic tissue specimens involving "skinny needle biopsies" and the use of fiber optic instruments, however, pathologists are often presented with tissue specimens of from about 10 to about 50 milligrams of tissue, which are much smaller than the large tissue "hunks" weighing from about 200 to about 2000 milligrams obtained from earlier surgical sampling methods. In order to obtain the maximum amount of information from only a few micro or milligrams of tissue, consecutively cut tissue sections are often treated with different histochemical reagents and histochemical tests are often repeated using slices taken at different depths within the tissue specimen. Thus, there is a currently a need to sort consecutively cut organic tissue sections into separate tissue ribbons and to control the sequence in which consecutively sliced tissue sections are added to each ribbon based on the logic of the histochemical analysis to be performed. Generating multiple tissue ribbons having a controlled sequencing is not possible using known microtomes in which each cut is made at the same position along the length of the cutting blade and only a single ribbon can be generated at a time.

Another known shortcoming of known microtomes providing only two-dimensional movement is that each consecutive intersection of the tissue specimen with the cutting edge of the blade is always made with the same segment of the cutting edge or a limited number of segments depending on the blade length. A typical 120 mm blade would provide an average of about 3 to 5 new cutting surfaces by shifting the blade in its clamp. The blade must be replaced as soon as the operative segments become nicked or dull. Further, known microtome blades are generally clamped into a heavy metal microtome blade carrier that fits properly into the various designs of commercial microtomes. Changing or shifting the blade requires releasing a screw or cam lock device on the blade carrier and disposing the used blade in a proper medical waste container. Changing or shifting the blade thus may be time consuming and requires handling of the blade itself. Since the blades are utilized to cut tissue sections made from potentially contaminated human tissue materials, technicians risk being infected with Hepatitis, AIDS, Tuberculosis or similar diseases by bacteria and viruses present on the cutting edge of the used blades.

Thus there is also a need to reduce the frequency of blade changes by providing a microtome cutting blade that is capable of being advanced in the direction parallel to the length of the blade to provide a fresh portion of the cutting edge at the cutting area of the microtome when the operative segment of the cutting edge becomes nicked or dull. There is a further need to provide a microtome cutting blade which is housed in a chamber or cartridge which may be disposed of in a contaminated medical waste system without exposing the technician to the cutting edge of the blade.

It is an object of the present invention to provide a method for automatically sorting tissue sections consecutively cut in a microtome from a tissue specimen into a plurality of tissue ribbons. Another object of the present invention is to provide a microtome having a cutting blade which is advanceable in the direction parallel to the direction of the length of the blade to expose a fresh segment of the cutting edge to the cutting area of the microtome.

A further object of the present invention is to provide an advanceable microtome cutting blade cartridge system which protects technicians from exposure to the cutting edge of the blade during handling.

SUMMARY OF THE INVENTION

In accordance with the present invention, multiple ribbons of tissue sections are generated from an organic tissue specimen by adding consecutively cut tissue sections in a desired sequence to the tissue ribbons being generated. A three-dimensional microtome is used to generate the tissue sections at various preselected positions along the length of the cutting blade by the intersection of the organic tissue specimen with the cutting edge of the blade at each of the preselected positions. More particularly, for each tissue ribbon desired, a cutting position is selected along the Z directional length of the cutting blade. A desired number of tissue sections are cut at a first cutting position, the organic tissue specimen is translated along the Z axis to any other preselected cutting position where additional tissue sections are cut. A cycle of cutting the tissue specimen followed by translating the tissue specimen along the length of the blade is repeated using any desired sequence of cutting positions and making any desired number of cuts at each position. By practicing this method, a plurality of tissue ribbons may be generated containing any desired sequencing of tissue sections.

The practice of the foregoing method is made possible by means of a microtome having driven guides in three dimensions for moving the organic tissue specimen in the X, Y, and Z axis directions. A control system controls the position of the tissue sample relative to the cutting blade prior to each cut, thereby allowing multiple ribbons of any desired thickness and tissue section sequence to be generated automatically from an organic tissue specimen.

In another embodiment of the present invention, the microtome includes an advanceable cutting blade apparatus capable of supplying a fresh cutting edge to the cutting area of the microtome when the operative portion of the cutting edge becomes nicked or dull. The cutting blade apparatus includes a cartridge containing a supply spindle and a takeup spindle each having an end of a continuous flexible cutting blade attached thereto. The cutting blade is wound around the supply and takeup spindles and has a portion exposed outside of said cartridge at the cutting area of the microtome. A means for rotating the supply and takeup spindles is provided which allows the blade to be advanced across the cutting area of the microtome to provide a fresh cutting edge to the cutting area as required. The cutting blade cartridge greatly reduces the frequency of required blade changes and protects technicians from exposure to the potentially contaminated cutting edge of the cutting blade.

BRIEF DESCRIPTION OF THE DRAWINGS

This invention will be more fully understood, and further objects and advantages thereof will become apparent in the following detailed description of preferred embodiments of the invention illustrated in the accompanying drawings, wherein like elements are referenced alike.

DETAILED DESCRIPTION OF THE PREFERRED EMBODIMENT

Figure 1:
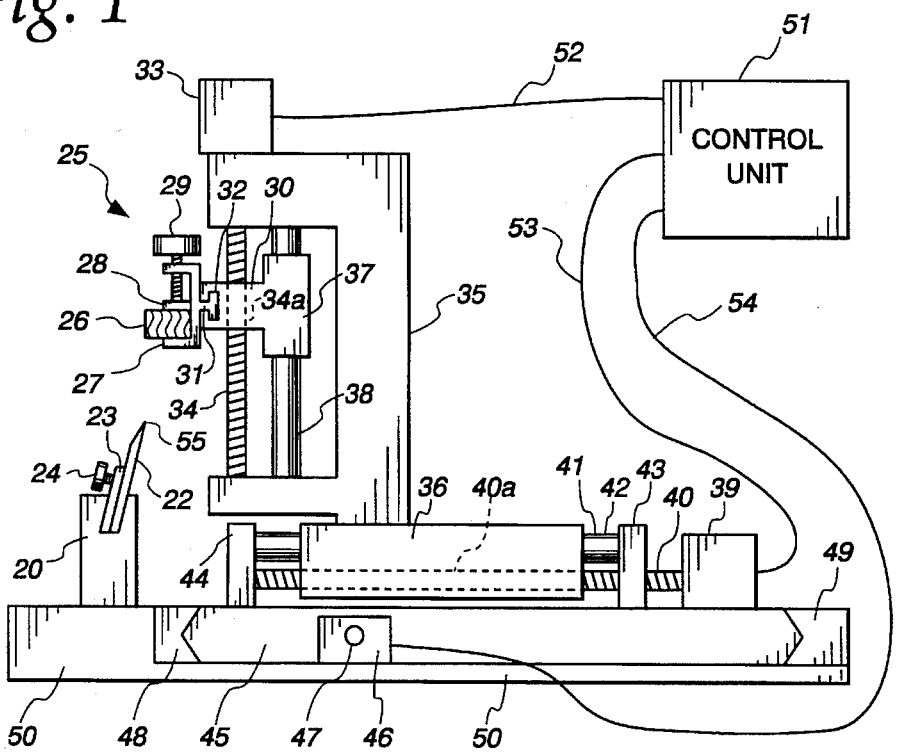
FIG. 1 is an elevational view of a multi-dimensional microtome apparatus constructed in accordance with the present invention.
Figure 2:
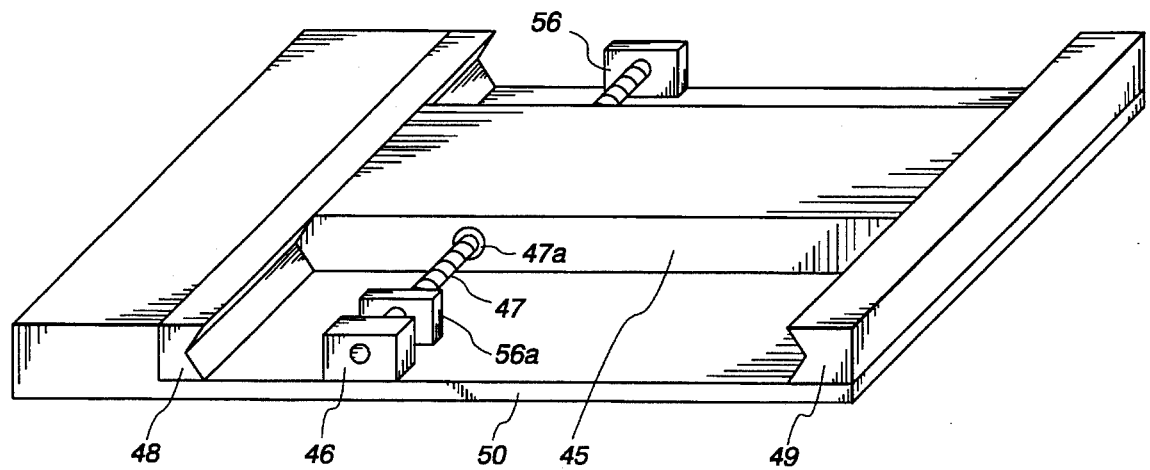
FIG. 2 is a view illustrating further details of the microtome apparatus shown in FIG. 1.

The multi-dimensional microtome shown in FIGS. 1 and 2 includes a blade holder 20 mounted on a base 50. A cutting blade 22 is removably mounted on the blade holder 20 by means of clamping plate 23 and thumbscrews 24. A specimen holding mechanism 25 holds an organic tissue specimen 26 by means of specimen clamps 27 and 28 and thumbscrew 29. The specimen holding mechanism 25 is removably connected to a specimen guide arm 30 by means of a dovetail heel 31 which slides in a linear dovetail 32 in the specimen guide arm 30. The specimen holding mechanism 25 and guide arm 30 are translatable vertically in the x direction and may be driven by a servo motor 33 which rotates a linear power screw 34 in a nut 34a in the guide arm. The servo motor 33 is mounted on a bracket 35 which is secured to a horizontal carriage 36 for horizontal movement. A slide 37, connected to the other end of the specimen guide arm, is slidably mounted on an x-axis guide post 38 for vertical sliding movement on the guide post. The latter is parallel to the linear screw 34 and acts in cooperation therewith to guide the organic tissue specimen 26 to travel only in the vertical x direction. Thus, as the motor 33 turns the screw 34 in the nut 34a the specimen holding mechanism 25 shifts the specimen thereon in the vertical or x direction.

The specimen holding mechanism 25 is carried on the horizontal carriage 36 and moves in unison therewith in its travel in the y direction. Translational movement of the horizontal carriage 36 in the y direction may be effected by a servo motor 39 through a linear power screw 40, which extends through a nut 40a mounted in the horizontal carriage, and which drives the carriage along y-axis guide posts 41 and 42. The y-axis guide posts and the linear power screw 40 are parallel to each other and are mounted at opposite ends in tail plates 43 and 44. Thus, as servo motor 39 rotates the screw 40 in the nut 40a the horizontal carriage shifts the specimen holding mechanism 25 and the specimen thereon in the horizontal y direction.

The specimen holding mechanism 25 also moves in unison with support plate 45 which translates in the horizontal z direction and may be driven by servo motor 46. The servo motor 46 drives a linear power screw 47, which is rotatably mounted at its opposite ends in horizontal parallel tail plates 56 and 56a (FIG. 2). The screw 47 extends through a nut 47a in the support plate 45. The support plate moves along z-axis guides 48 and 49 which are connected to the base 50 and prevent movement of the support plate in the x and y directions. Thus, as the motor 46 turns the screw 47 in the nut 47a, the support plate shifts the specimen holding mechanism 25 and the specimen 26 thereon in the horizontal z direction.

The servo motors 33, 39, and 46 are connected to a control unit 51, by leads 52, 53, and 54, respectively. The control unit controls the three servo motors in response to operator input or a pre-programmed control source to provide movement of the specimen holding mechanism in the x, y, and z directions. The control unit is shown generally in FIG. 1 and is meant to be indicative of the variety of ways the three-dimensional microtome could be controlled by one skilled in the art. Any other suitable controller would be appropriate.

Actual means of translating the specimen holding mechanism 25 in the x, y and z directions are not limited to the linear power screws shown in FIGS. 1 & 2, but may include other known devices such as belts and pulleys or linear shafts adapted for providing linear translation. Furthermore, translational movement of the specimen holding mechanism in any of these directions may be effected manually, such as by crank action drives, in place of the servo motors described above.

With the organic tissue specimen 26 mounted in the specimen holding mechanism 25, tissue sectioning is effected by first adjusting the tissue specimen to a desired initial position. Servo motor 33 is operated to position the tissue specimen vertically above the cutting edge 55 of cutting blade 22. It is preferable to first position the tissue specimen above the cutting edge so that subsequent horizontal movements may be accomplished without causing contact between the tissue specimen 26 and the cutting blade 22 or the cutting edge 55. Servo motor 39 may then be operated to adjust the initial position of the tissue specimen in the y direction relative to the stationary blade to expose a section of the tissue specimen of a desired thickness to the cutting edge of the cutting blade. The initial position of the tissue specimen in the z direction along the cutting blade may also be adjusted by operation of servo motor 46. Once the organic tissue specimen 26 is located at its desired initial position, servo motor 33 is turned in a first direction to translate the tissue specimen downward in the x direction from a position above the cutting edge 55 to a position below the cutting blade causing the specimen to be sliced as it intersects the cutting edge of the blade. In the preferred method, servo motor 39 is employed after each section is cut to retract the tissue specimen away from the blade in the y direction a distance sufficient to avoid contact between the tissue specimen and the cutting blade during subsequent movements of the tissue specimen in the x and z directions.

After the initial section of the organic tissue specimen has been cut and the specimen has been retracted from the cutting blade as described above, the specimen is raised in the x direction, by turning the servo motor 33 to raise the specimen to a position above the cutting edge 55. It is generally not critical how far above the cutting edge 55 the tissue specimen 26 is repositioned as differences in this distance will affect only the cutting frequency. Once the tissue specimen 26 is positioned vertically above the cutting edge 55, it is translated horizontally in the y direction towards the blade by means of servo motor 39 to adjust the thickness of the second tissue section cut.

If desired, the second organic tissue section may be cut with a different segment of the cutting blade than the segment used to cut the preceding specimen by repositioning the tissue specimen in the z direction by operation of the servo motor 46 before the second cut is made. Each time the tissue specimen is sectioned at a new position along the cutting blade, formation of a new tissue ribbon is initiated. Sufficient distance should be provided between adjacent cutting positions to avoid overlap of the adjacent tissue ribbons generated. The order of x and z directional movement is optional.

Once the organic tissue specimen has been repositioned as described above, the second tissue section is cut by again translating the specimen downward in the x direction to cause the specimen to intersect the cutting edge 55 of the cutting blade 22 at the desired point along the blade. After this cut has been made, the specimen is again retracted and repositioned by means of the servo motors, as described above, until a desired number of tissue sections have been cut from the tissue specimen 26 at a desired number of cutting positions along the blade. In the preferred embodiment, the entire sequence of positional movements required to cut the desired number of sections from a given tissue specimen is controlled by the control unit 51 based on operator input or a programmed control sequence.

Alternatively, repositioning the tissue specimen in the z direction may be omitted and the second cut can be made with the same segment of the cutting blade as the preceding cut.

Figure 3:
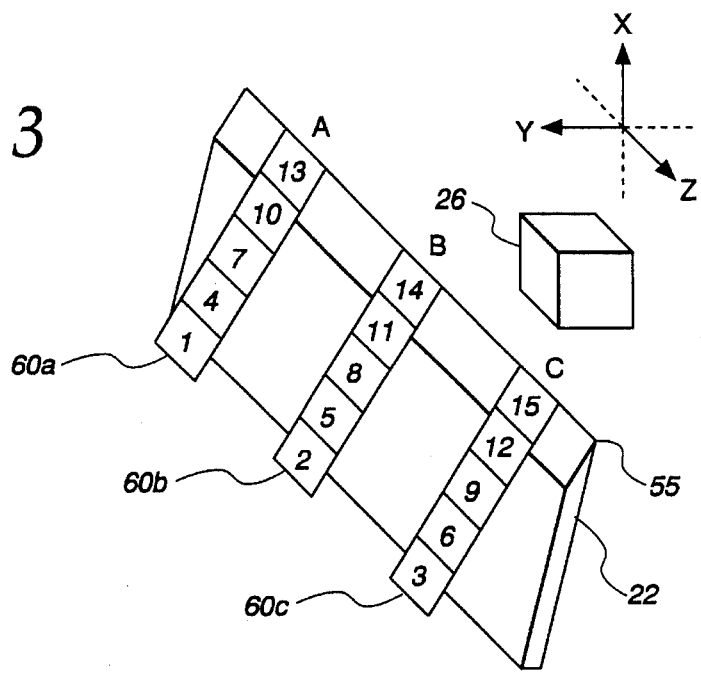
FIG. 3 is a perspective view of sequenced tissue ribbons produced according to a method of the present invention.

FIG. 3 shows a perspective view of the organic tissue specimen 26 and cutting blade 22 of the present microtome for purposes of further clarifying the practice and advantages of the present invention. As shown in FIG. 3, individual tissue sections cut at the same position in the z direction along the cutting blade 22 tend to adhere to each other end to end to form ribbons of tissue sections. A principle feature of the present apparatus and method, is that multiple tissue ribbons may be adjacently generated from an organic tissue specimen by cutting the tissue specimen at multiple predetermined positions along the length of the cutting blade 22. Three such tissue ribbons generated at three distinct positions along the length of cutting blade 22 are shown in FIG. 3 as 60a, 60b, and 60c. The sequence in which consecutively cut tissue sections are added to each of the tissue ribbons being generated may be controlled by translating the tissue sample to the next desired z directional cutting position before each cut is made. By allowing complete control of the position at which each consecutive cut is made, the present invention allows multiple tissue ribbons of any desired tissue section sequencing to be generated.

Figure 4A:
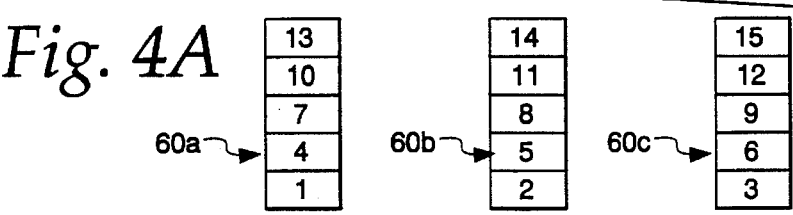
FIG. 4 is an illustration of various tissue ribbon sequences made possible by the method and apparatus of the present invention.
Figure 4B:
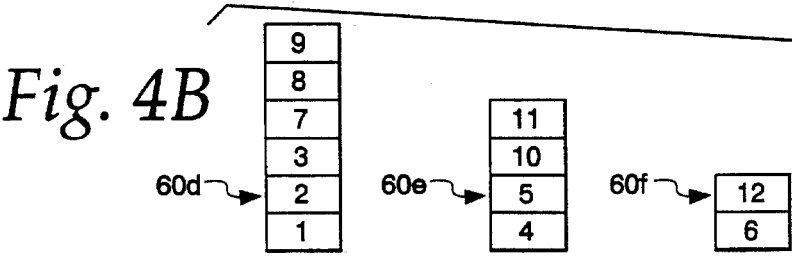

In accordance with the present method, tissue ribbons such as those shown in FIG. 3 may be generated by cutting a first tissue section 1 in FIG. 3 at a first position A by the method described above, translating the tissue sample in the z direction to a second position B, cutting a tissue section 2 at second position B, translating the tissue specimen in the z direction to a third position C, cutting a third tissue section 3 at position C, translating the tissue sample in the z direction back to the first position A, and repeating these steps until tissue sections 1 through 15 have been generated. Consecutive tissue sections cut at the same z axis position along the cutting blade will adhere to each other forming tissue ribbons 60a, 60b, and 60c. In the preferred embodiment, the desired tissue sections are automatically generated by the control unit 51 which executes the required sequence of x, y, and z directional tissue specimen movement through manipulation of servo motors 33, 39, and 46. The sequencing of the tissue ribbons generated by the present invention is not limited to that of the tissue sections described in FIG. 3. Ribbons of any desired tissue sequence may be generated by simply alternating the sequence of movements entered into control unit 51 as required. FIG. 4 illustrates other examples of possible tissue sequencing which may be chosen to best accommodate the histological analysis to be performed on the tissue sections. The "3 Channel Consecutive" sequence illustrated by tissue ribbons 60a, 60b, and 60c in FIG. 4A corresponds to the ribbons formed according to the sequence of cuts described in FIG. 3. Alternatively, a "3-2-1 Ratio Consecutive" sequence could be utilized to generate the tissue ribbons 60d, 60e, and 60f shown in FIG. 4B by repeating a cycle of cutting three consecutive tissue sections 1, 2, and 3 at a first desired cutting position, followed by shifting the specimen in the z direction and cutting two consecutive tissue sections 4, and 5 at a second desired cutting position, followed by shifting the specimen in the z direction and cutting one tissue section 6 at a third desired cutting position. As one of skill in the art would recognize that numerous other algorithms could be chosen to generate any desired tissue section sequence simultaneously from the same tissue specimen according to the present invention.

Further, the number of tissue ribbons that may be generated adjacent to one another along the length of the cutting blade may vary considerably, the maximum number being limited by the following formula:

$$N=(L+D)/(W+D)$$

Where:

N=The maximum number of tissue ribbons capable of being generated adjacent to one another.

L=The z directional length of the cutting blade exposed at the cutting area of the microtome.

D=The desired z directional distance between adjacent tissue ribbons.

W=The z directional width of the tissue specimen to be cut.

Figure 4C:
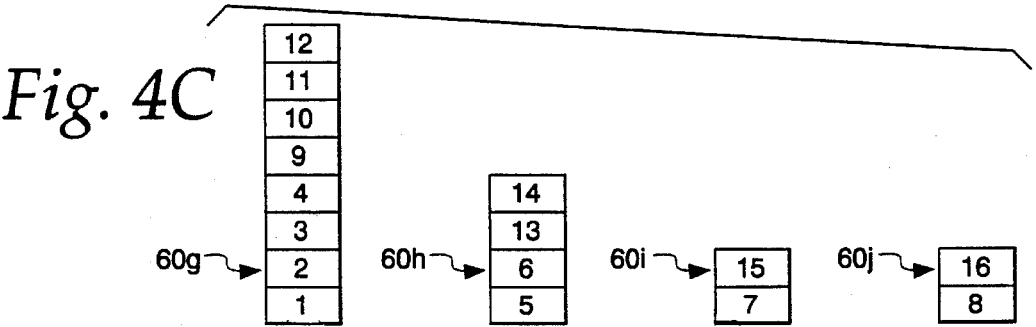

FIG. 4C illustrates a "4-2-1-1 Ratio Consecutive" sequence in which four separate tissue ribbons 60g–60j are generated by making cuts at four distinct z directional positions in the sequence indicated.

It will be understood that the method of the present invention may also be practiced by translating the cutting blade in the direction of its length in between cuts to expose the tissue specimen to a different segment along the blade. Movement of the tissue specimen is preferred however over movement of the blade to avoid disruption of the tissue ribbons being generated on the blade.

Thus, according to the present invention a method is provided for generating a plurality of section sequenced tissue ribbons from an organic tissue specimen using a microtome having a cutting blade whose length is oriented along a z axis. According to the method of the invention, a desired number of tissue sections of an organic tissue specimen are cut at a first position along the length of the cutting blade, relative movement between the organic tissue specimen and the cutting blade is provided in the direction parallel to the length of the cutting blade to arrive at a next desired cutting position along the length of the cutting blade, a desired number of sections of the organic tissue specimen are cut at the next desired cutting position, and these steps are repeated as desired to form the multiple tissue ribbons.

Figure 5:
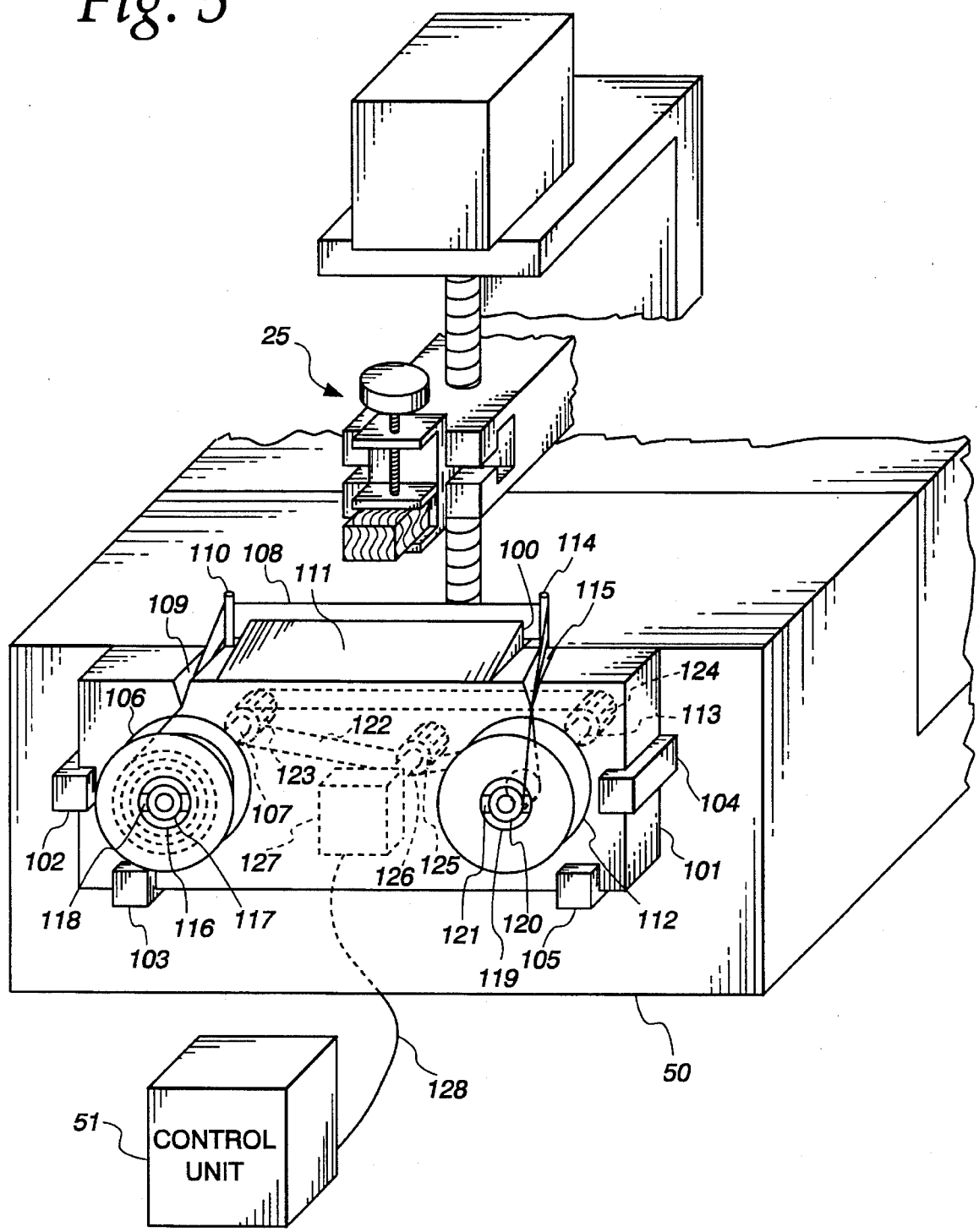
FIG. 5 is elevational view of an alternative embodiment of the microtome of FIGS. 1 and 2 containing an advanceable cutting blade apparatus.

FIG. 5 is an elevational view of another embodiment of the three-dimensional microtome of the present invention in which the cutting blade 22, and cutting blade holder 20 shown in FIG. 1 are replaced by an advanceable cutting blade cartridge 101 which is mounted on the face of a base 50 which corresponds to the base 50 in the first embodiment of the invention. The specimen holding mechanism 25 is carried by the horizontal carriage 36, as above described. The cartridge 101 is preferably formed from a lightweight disposable plastic material. The cartridge 101 may be releasably secured to the face of base 50 by means of releasable clamps 102, 103, 104, and 105.

A supply spool 106 is rotatably mounted within the cartridge 101. When the cartridge is positioned within the releasable clamps, an axle 107 extends into the center bore 116 of supply spool 106. The axle 107 has tabs 117 for cooperation with the grooves 118 in center bore 116 allowing the supply spool 106 to rotate with the axle 107.

An advanceable cutting blade 108 is connected at one end to the supply spool 106 and is wound around the supply spool in the shape of a disc. The advanceable cutting blade 108 exits the cartridge 101 through a slot 109 and extends around a ninety degree twist guide 110 to the cutting area of the microtome. The portion of the advanceable cutting blade within the cutting area of the microtome may be reinforced by means of a reinforcement plate 111 which contains a groove 100 within which the advanceable cutting blade is interposed. The reinforcement plate 111 supports the cutting blade within the cutting area to prevent the blade from bending or folding during the cutting operation. Alternatively, the necessary rigidity of the advanceable cutting blade within the cutting area may be by provided by controlling the tension of the segment of the blade which spans the cutting area.

Takeup spool 112 is also rotatably mounted within the cartridge 101. An axle 113 extends into the center bore 119 of the takeup spool. The axle 113 has tabs 120 for cooperation with the grooves 121 in center bore 119 allowing the takeup spool 112 to rotate with the axle 113. At the other end of the cutting area of the microtome, the advanceable cutting blade 108 extends around a second ninety degree twist guide 114, and reenters cartridge 101 through slot 115. The cutting blade is attached at its other end to the takeup spool 112.

Translation of the cutting blade 111 across the cutting area of the microtome is effected by rotation of the supply and takeup spools in cooperation with each other. A slotted belt 122 extends around sprockets 123 and 124, which are attached to the ends of axles 107 and 113 respectively, and also around sprocket 125 attached to the end of axle 126. Rotation of axle 126 may be driven by servo motor 127, which may be controlled by control unit 51 in response to operator input or preprogrammed commands. The servo motor 127 is electronically connected to the control unit 51 by means of leads 128. Alternatively, various arrangements of gears could be employed in place of the belt drive just described, or the supply spool 106 and takeup spool 112 could be driven by separate motors instead of employing belt or gear mechanisms. The cutting blade 111 could also be advanced manually such as by replacing servo motor 127 with a crank drive.

The advanceable cutting blade for use in this embodiment of the present invention is preferably formed from a flexible strip of metal having dimensions of from about 0.005 to about 0.015 inches thick and from about 0.100 to about 0.300 inches wide and any desirable length which may be packed onto the supply spool. The advanceable cutting blade may be formed from stainless steel hardened to Rockwell 60–70. The blade surface may be treated with nitrate, chromate, Teflon or other suitable materials to improve its durability and cutting characteristics. Other suitable non-metallic materials such as ceramic coatings could also be used. One end of the strip is honed to a razor sharp edge to form the cutting edge of the blade. The blade is preferably lubricated with a suitable lubricant to prevent corrosion during storage and periods of non-use.

Various alternative geometric arrangements for the placement of the advanceable cutting blade system shown in FIG. 5 could also be employed. For, instance, the cartridge 101 could be mounted on top of the base 50.

A further advantage of the advanceable cartridge blade system shown in FIG. 5 is that when the entire length of the advanceable blade has been used, the cartridge may be conveniently removed from the microtome and disposed of in a suitable medical waste disposal container by releasing clamps 102, 103, 104 and 105 without the need to touch or handle the actual cutting blade itself. Thus, the cartridge blade protects the technician from exposure to disease causing bacteria or virus organisms potentially present on the surface of the blade. One of skill in the art would recognize, however, that the present invention is not limited to the cartridge blade system just described, but includes various other embodiments of microtome blades that are capable of being conveniently advanced across the cutting area of the microtome without having to unclamp the blade to provide a fresh cutting edge.

While the present invention has been described with reference to its preferred embodiments, it will be understood to those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for generating parallel tissue ribbons from an organic tissue specimen comprising:
   (a) providing a base;
   (b) providing a cutting blade mounted on the base for cutting sections from the tissue specimen;
   (c) providing a tissue specimen holder mounted on the base for holding a tissue specimen;
   (d) shifting the tissue holder relative to the cutting blade in a first direction to cause the cutting of a first tissue section from the tissue specimen at a first cutting location;

(e) shifting the specimen holder relative to the cutting blade in a second direction perpendicular to the first direction to present a second section of the tissue specimen for cutting at a second cutting location spaced in the second direction from the first cutting location to cut a second tissue section; and (f) shifting the tissue specimen in a third direction to bring the tissue specimen over the cutting blade to cut an additional tissue section joined to the first tissue section to form a first tissue ribbon with multiple tissue ribbon sections and to bring the tissue specimen to cut an additional tissue section joined to the second tissue section to form a second tissue ribbon.

2. A method for generating a plurality of section sequenced tissue ribbons from an organic tissue specimen using a microtome having three-dimensional movement for sectioning tissue specimens, the method comprising:

(a) providing a base;

(b) providing a cutting blade mounted on the base and having a length parallel to a Z axis;

(c) providing a holding means connected to the base for holding the organic tissue specimen to be cut by the cutting blade;

(d) driving the organic tissue specimen along an X axis perpendicular to the Z axis to cut a section of tissue from the tissue specimen at a first cutting position;

(e) driving the organic tissue specimen along a Y axis perpendicular to the X and Z axes to present a next section of the tissue specimen to be cut;

(f) driving the tissue specimen along the Z axis to reposition the tissue specimen at a location spaced in the Z direction from the first cutting position.

3. A method for generating a plurality of section sequenced tissue ribbons from an organic tissue specimen using a microtome having a cutting blade whose length is oriented along a z axis, the method comprising:

(a) cutting a desired number of sections of the organic tissue specimen at a first position along the length of the cutting blade;

(b) providing relative movement between the organic tissue specimen and the cutting blade in the direction parallel to the length of the cutting blade to arrive at a next desired cutting position along the length of the cutting blade;

(c) cutting a desired number of sections of the organic tissue specimen at the next desired cutting position;

(d) repeating steps (b) and (c) a desired number of times, wherein the relative movement required in step (b) is provided by traversing the organic tissue specimen along the length of the cutting blade in the Z direction while holding the cutting blade stationary.

4. The method of claim 3 wherein the maximum number of tissue ribbons N spaced a distance D apart along the length of the cutting blade are formed from a organic tissue specimen having a width W using a microtome having a cutting area of length L, the maximum number of tissue ribbons N being calculated by the formula:

$$N=(L+D)/(W+D).$$

5. A microtome for generating parallel tissue ribbons from an organic tissue specimen comprising:

(a) a base;

(b) a cutting blade mounted on the base for cutting sections from the tissue specimen;

(c) a tissue specimen holder mounted on the base for holding a tissue specimen;

(d) means on the base for shifting the tissue holder relative to the cutting blade in a first direction to cause the cutting of a first tissue section from the tissue specimen at a first cutting location;

(e) means on the base for shifting the specimen holder relative to the cutting blade in a second direction perpendicular to the first direction to present a second section of the tissue specimen for cutting at a second cutting location spaced in the second direction from the first cutting location to cut a second tissue section; and (f) means on the base to shift the tissue specimen in a third direction to bring the tissue specimen over the cutting blade to cut an additional tissue section joined to the first tissue section to form a first tissue ribbon with multiple tissue ribbon sections and to bring the tissue specimen to cut an additional tissue section joined to the second tissue section to form a second tissue ribbon.

6. A microtome having three-dimensional movement for sectioning organic tissue specimens comprising:

(a) a base;

(b) a cutting blade mounted on the base and having a length parallel to a Z axis;

(c) a holding means connected to the base for holding the organic tissue specimen to be cut by the cutting blade;

(d) a first drive means mounted on the base for driving the organic tissue specimen along an X axis perpendicular to the Z axis to cut a section of tissue from the tissue specimen at a first cutting position;

(e) a second drive means mounted on the base for driving the organic tissue specimen along a Y axis perpendicular to the X and Z axis to present a next section of the tissue specimen to be cut;

(f) a third drive means mounted on the base for driving the tissue specimen along the Z axis to reposition a next section of the tissue to be cut at a location spaced in the Z direction from the first cutting position.

7. The microtome of claim 6 further comprising a control means for controlling the movement and position of the organic tissue specimen along the X, Y, and Z axis according to operator input.

8. The microtome of claim 6 further comprising a control means for controlling the movement and position of the organic tissue specimen along the X, Y, and Z axis according to a preprogrammed control source.

9. The microtome of claim 6 wherein the cutting blade has a cutting edge and is capable of being advanced along the Z axis to expose fresh segments of the cutting edge of the cutting blade to a cutting area of a microtome.

10. The microtome of claim 1 wherein the fresh segments of the cutting edge are supplied to the cutting area by means of a cutting blade apparatus comprising: a cartridge, a supply spindle and a takeup spindle rotatably supported within the cartridge, a cutting blade having ends connected to the supply and takeup spindles, the cutting blade being capable of winding around the supply and takeup spindles and having a portion exposed outside of the cartridge, and rotating means for rotating the supply and takeup spindles thereby advancing the cutting blade from the supply spindle to the takeup spindle.

11. The microtome of claim 10 further comprising a reinforcing means for reinforcing the exposed portion of the cutting blade at the cutting area of the microtome.

12. The microtome of claim 10 wherein the cartridge containing the supply and takeup spindles and the cutting blade is removably mounted on the microtome to allow disposal of the cartridge.

13. The microtome of claim 9 further comprising control means for controlling the advancement of the cutting blade according to operator input.

14. The microtome of claim 9 further comprising control means for controlling the advancement of the cutting blade according to a preprogrammed control source.

15. A microtome for sectioning organic tissue specimens to form multiple tissue sections at adjacent spaced positions comprising:
 (a) a base;
 (b) a cutting blade mounted on the base and including a cutting edge having a length extending in a first direction and capable of being advanced in a direction parallel to its length to expose fresh segments of the cutting edge of the cutting blade to a cutting area of the microtome;
 (c) a holding means mounted on the base for holding the organic tissue specimen to be cut by the cutting blade; and
 (d) the means mounted on the base for moving the organic tissue specimen towards and away from the cutting blade and in the first direction to a plurality of different spaced positions along the length of the cutting edge to generate multiple tissue sections at the different spaced positions.

16. The microtome of claim 15 wherein the fresh segments of the cutting edge are supplied to the cutting area by means of a cutting blade apparatus comprising: a cartridge, a supply spindle and a takeup spindle rotatably supported within the cartridge, a cutting blade having ends connected to the supply and takeup spindles, the cutting blade being capable of winding around the supply and takeup spindles and having a portion exposed outside of the cartridge, and rotating means for rotating the supply and takeup spindles thereby advancing the cutting blade from the supply spindle to the takeup spindle.

17. The microtome of claim 16 further comprising a reinforcing means for reinforcing the exposed portion of the cutting blade at the cutting area of the microtome.

18. The microtome of claim 16 wherein the cartridge containing the supply and takeup spindles and the cutting blade is removably mounted on the microtome to allow disposal of the cartridge.

19. The microtome of claim 15 further comprising control means for controlling the advancement of the cutting blade according to operator input.

20. The microtome of claim 15 further comprising control means for controlling the advancement of the cutting blade according to a preprogrammed control source.

21. A microtome having three-dimensional movement for sectioning organic tissue specimens comprising:
 (a) a base;
 (b) a cartridge removably mounted on the base;
 (c) a supply spindle and a takeup spindle rotatably supported within the cartridge;
 (d) a cutting blade having ends connected to the supply and takeup spindles, the cutting blade being capable of winding around the supply and takeup spindles and having a cutting portion exposed outside of the cartridge with the cutting portion extending along a longitudinal Z-axis;
 (e) rotating means capable of engaging the supply and takeup spindles for rotating the supply and takeup spindles thereby advancing the cutting blade from the supply spindle to the takeup spindle;
 (f) a holding means mounted on the base for holding the organic tissue specimen to be cut by the cutting blade;
 (g) a first drive means mounted on the base for driving the organic tissue specimen along an X axis perpendicular to the Z axis to cut a section of tissue from the tissue specimen at a first cutting position;
 (h) a second drive means mounted on the base for driving the organic tissue specimen along a Y axis perpendicular to the X and Z axes to present a next section of the tissue specimen to be cut;
 (i) a third drive means mounted on the base for driving the tissue specimen along the Z axis to cut a next section of the tissue at a location spaced in the Z direction from the first cutting position.

22. The microtome of claim 21 further comprising a reinforcing means for reinforcing the exposed portion of the cutting blade at a cutting area of the microtome.

23. The microtome of claim 21 further comprising a control means for controlling the movement and position of the organic tissue specimen along the X, Y, and Z axis according to operator input.

24. The microtome of claim 21 further comprising a control means for controlling the movement and position of the organic tissue specimen along the X, Y, and Z axis according to a preprogrammed control source.

25. The microtome of claim 21 further comprising control means for controlling the advancement of the cutting blade according to operator input.

26. The microtome of claim 21 further comprising control means for controlling the advancement of the cutting blade according to a preprogrammed control source.

* * * * *